United States Patent
Davis et al.

(10) Patent No.: US 6,274,324 B1
(45) Date of Patent: Aug. 14, 2001

(54) SPECIFIC BINDING REAGENT COMPRISING A VARIABLE DOMAIN PROTEIN LINKED TO A SUPPORT OR TRACER

(75) Inventors: Paul James Davis, Beds; Martine Elisa Verhoeyen, Northants; Ronald Frank Jacobus De Winter, Bedford, all of (GB)

(73) Assignee: Unilever Patent Holdings B.V., Rotterdam (NL)

( * ) Notice: Subject to any disclaimer, the term of this patent is extended or adjusted under 35 U.S.C. 154(b) by 0 days.

(21) Appl. No.: 08/226,376

(22) Filed: Apr. 12, 1994

Related U.S. Application Data

(63) Continuation of application No. 07/741,425, filed on Oct. 1, 1991, now abandoned.

(30) Foreign Application Priority Data

Dec. 1, 1989 (GB) .................................................. 8927230

(51) Int. Cl.[7] ........................ G01N 33/53; G01N 33/566; C07K 16/00
(52) U.S. Cl. ........................ 435/7.1; 435/69.1; 435/69.7; 435/70.3; 435/70.21; 435/71.1; 435/172.1; 435/173.3; 436/501; 436/512; 436/518; 436/536; 530/378.1; 530/387.3; 530/810; 530/866; 530/867
(58) Field of Search ........................ 435/68, 69.1, 69.6, 435/70, 172.1, 172.3, 252.3, 252.33, 240.2, 254, 255, 320, 7.1, 69.7, 70.2, 70.21, 71.1; 536/127; 530/387, 866, 867, 387.1, 387.3, 810; 535/15, 68, 69, 73, 74, 76; 436/501, 512, 518, 536

(56) References Cited

U.S. PATENT DOCUMENTS

| | | | |
|---|---|---|---|
| 4,671,958 | * | 6/1987 | Rodwell et al. ........................ 424/85 |
| 4,769,326 | * | 9/1988 | Rutter ...................................... 435/68 |
| 4,946,778 | * | 8/1990 | Ladner et al. ....................... 435/69.9 |

FOREIGN PATENT DOCUMENTS

| | | | |
|---|---|---|---|
| 253325A | * | 1/1988 | (EP) . |
| 0341498 | * | 11/1989 | (EP) . |
| 0 368 684 | | 5/1990 | (EP) .............................. C07K/13/00 |
| 88/09344 | * | 12/1988 | (WO) . |

OTHER PUBLICATIONS

Ward et al, Letters to Nature, vol. 341, pp. 544–546 (Oct. 1989).

* cited by examiner

*Primary Examiner*—Bennett Celsa
(74) *Attorney, Agent, or Firm*—Pillsbury Winthrop LLP

(57) ABSTRACT

Small specific binding molecules, such as single variable domain antibodies (Dabs) and Fv fragments, can be coupled to solid plastics surfaces or to tracers such as enzymes by means of linkers comprising polypeptides containing from 5 to 20 amino acids and which are hydrophobic and/or contain at least one lysine residue. The coupling can be achieved without significant loss of specific binding activity. The combined Dab/linker or Fv/linker can be prepared by expression in genetically-modified organisms.

14 Claims, 3 Drawing Sheets

I:
```
               homology              Kpn1                    EcoR1
        5' TAG CCC TTA TTA CAG GTA CCC CTT ACC GGA ATT CCC (GCT ACC)n
           BamH1    homology
           GGA TCC TGA GGA GAC GGT 3'                                    n=0-5
```

II:
```
            homology            Kpn1
        5' TAG CCC TTA TTA CTT CAG GTA CCC CTT ACC GGA GTT CCC (GCT ACC)n
           Bam HI   homology
           GGA TCC TGA GGA GAC GGT 3'                                    n = 0-5
```

III:
```
            homology            Kpn1                                      Sac II
        5' TAG CCC TTA TTA GGG TAC CAA AAG CTT CGC (AAG TGC)n TAC CGC GGC
           homology
           TGA GGA GAC GGT 3'                                             n = 0-5
```

*Fig.1.*

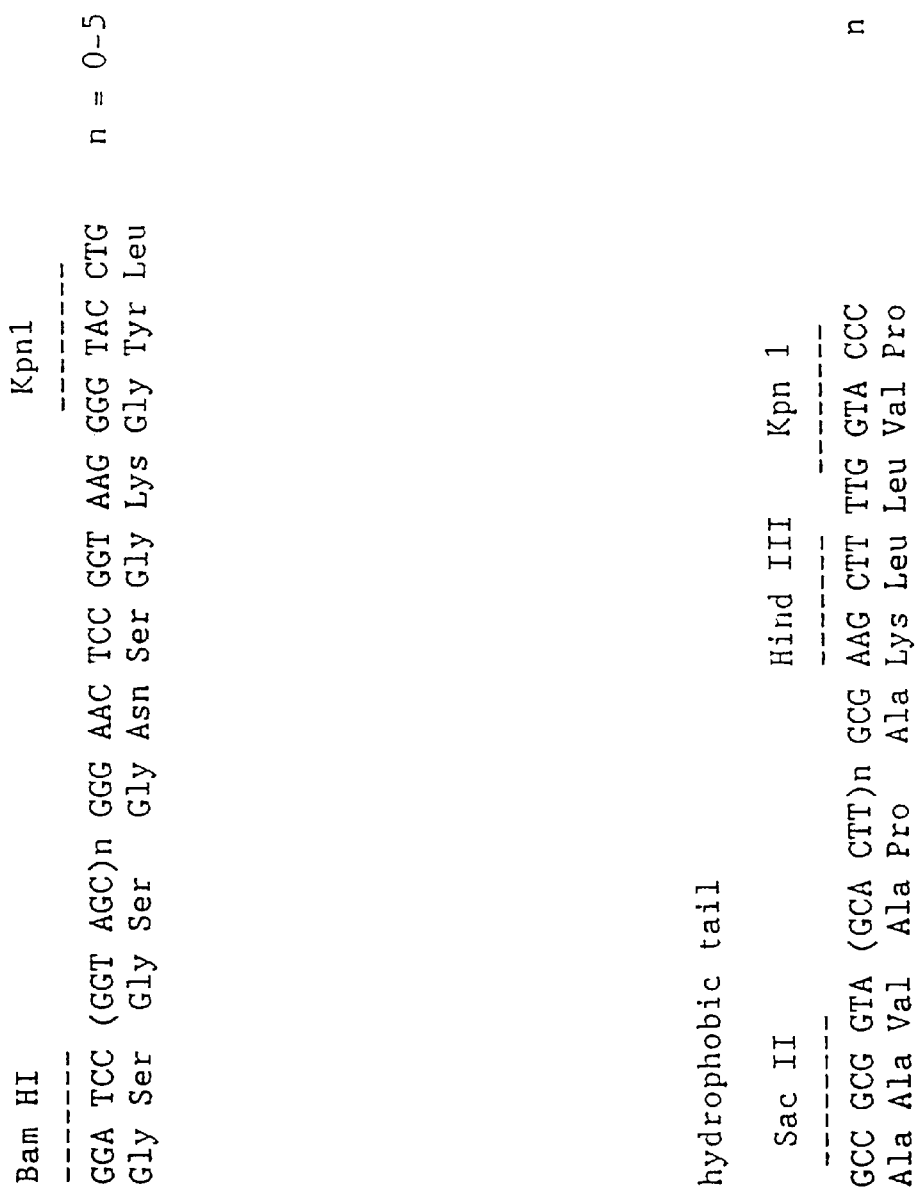

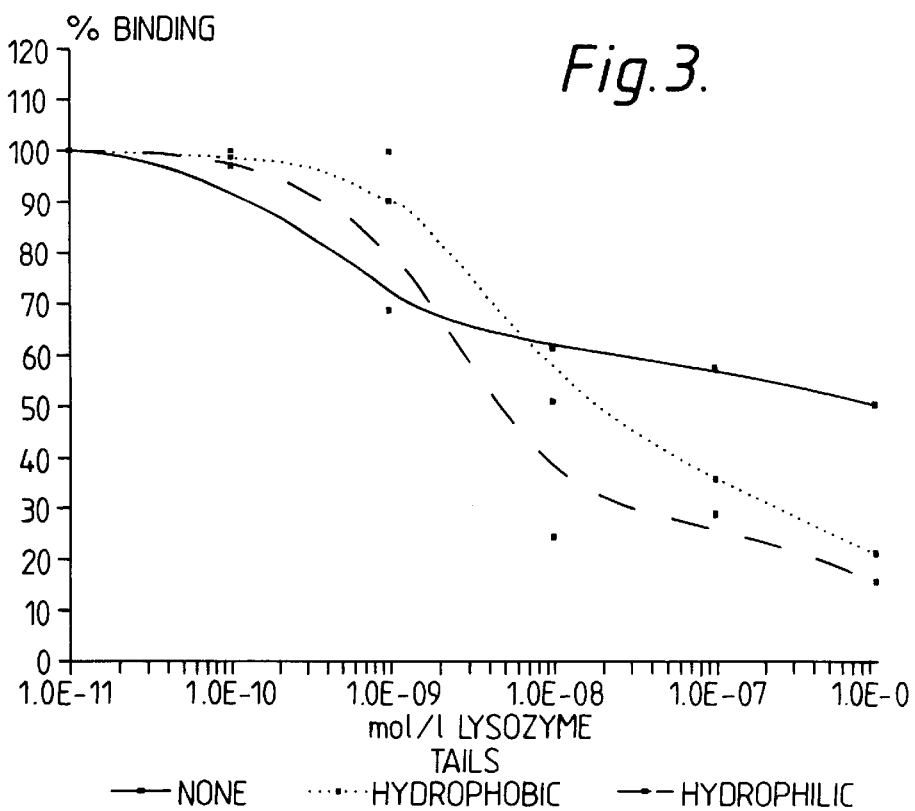
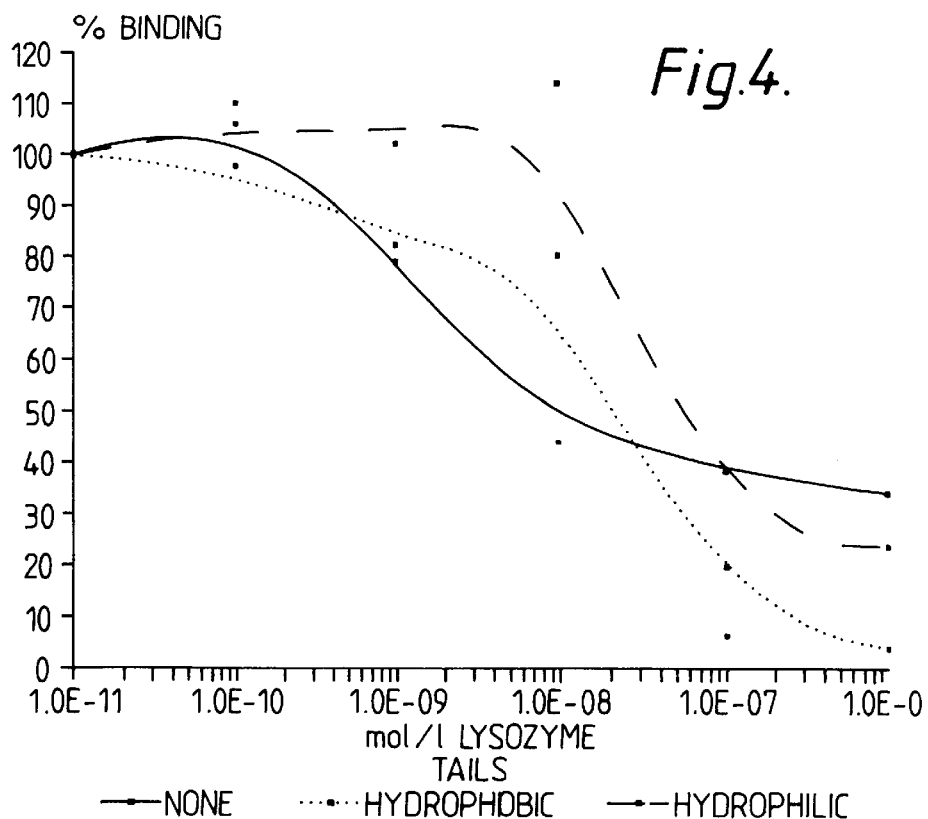

US 6,274,324 B1

SPECIFIC BINDING REAGENT COMPRISING A VARIABLE DOMAIN PROTEIN LINKED TO A SUPPORT OR TRACER

This is a continuation of application Ser. No. 07/741,425, filed on Oct. 1, 1991, which was abandoned upon the filing hereof.

This invention relates to reagents having specific binding properties. The invention relates in particular to reagents comprising a specific binding agent linked to a solid surface or linked to a tracer.

BACKGROUND OF THE INVENTION

Natural antibodies, either polyclonal or monoclonal, have been used widely as specific binding agents. When immobilised on solid phases, such as pegs, dip-sticks, wells and moisture-permeable membranes such as filters and strips, or when linked to various tracers (otherwise known as labels or markers), they can be used in assays.

Antibodies are large complex multi-chain proteinaceous structures. Although it has been appreciated for some while that substantial portions of these structures seem unrelated to the specific binding properties, the minimum portion necessary to provide adequate specific binding has been a matter of debate. It has already been shown that so-called Fv fragments, ie. an antibody fragment essentially comprising only a single heavy-chain variable region and its corresponding light chain variable region, can exhibit specific binding activity. Very recently it has also been shown by Ward et al (*Nature*, 1989, Vol. 341, p.544–546) that a single variable domain from an antibody can exhibit significant specific binding activity. The production of single variable domain antibodies (Dabs), as described by Ward et al, is also described in detail in EP 0368684 A1 (Medical Research Council) published on May 16, 1990.

To be of practical use in immunoassays, specific binding activity alone is not sufficient. The specific binding agent must also be capable of being linked to other material, for example a label such as an enzyme or a particle, or to a solid phase. This linkage must be achievable without any significant adverse effect on the specific binding activity. Such adverse effects can easily arise through chemical or conformational changes in the specific binding region, or simply by physical (stearic) hindrance of access to the specific binding region. In the case of conventional specific binding reagents, ie. whole antibody molecules or large portions of such molecules such as Fab fragments, the specific binding region or regions comprise only a minor proportion of the total molecule. The comparatively vast residual bulk of the molecule, which is apparently not directly involved in the specific binding activity, provides abundant scope for the existence of locations which can participate in chemical or physical linkage with other materials such as labels and solid phases. These regions can be relatively remote from the essential specific binding regions, and the resulting linkages need not interfere with the specific binding activity.

However, in the case of a specific binding entity essentially comprising only one or more variable domains unassociated with any substantial portion of the originating antibody or antibodies, eg. a Fv fragment or a single variable domain (Dab), the relative proportion of the molecule which participates in the essential specific binding activity is very much higher. Indeed, it would be expected that any attempt to link the small specific binding entity to another material will entail a very high risk that the essential specific binding activity will be adversely affected.

SUMMARY OF THE INVENTION

An objective of the present invention is to facilitate the linking of such small specific binding entities to other useful materials with less risk of damage to their essential specific binding properties.

DESCRIPTION

The invention provides a specific binding reagent, comprising:
i) one or more variable domain proteins ($V_H$ and/or $V_L$ unassociated with any substantial portion of originating antibody or antibodies;
ii) a linking group, which does not contribute to the specific binding properties of the reagent, comprising at least 5 amino acid residues, and which is hydrophobic and/or includes at least one lysine residue, the coupling properties of the linking group thereby being enhanced; and
iii) a solid surface or a tracer, coupled via the linking group to the variable domain protein(s).

DESCRIPTION OF PREFERRED EMBODIMENTS

For the purposes of this specification, the "reagent" of the invention may be a water-soluble or water-dispersible material, or may be a solid device such as a bead, peg, dip-stick, or well or other container, having a surface on which the variable domain protein(s) are immobilised by means of the linking group.

Preferably the linking group comprises not more than 20 amino acid residues. Preferably the linking group is hydrophobic and includes at least one lysine residue. The presence of a lysine residue provides a very convenient site for covalent attachment to proteinaceous tracers, such as enzymes.

To provide the linking group with sufficient hydrophobicity to achieve the purposes of the invention, the polypeptide chain comprising the linking group should is contain a sufficient number (which may be as few as two, if the residues are adjacent) of amino acid residues selected from the group consisting of valine, leucine, iso-leucine, phenylalanine, tyrosine, tryptophan, proline and alanine. We have found that even if the majority of the amino acid residues in the polypeptide are other, relatively polar (and hence relatively hydrophylic), amino acid residues, the presence of merely a low proportion of residues from the above group can confer effective hydrophobicity on the polypeptide. The hydrophobic region or regions can be adjacent to regions of high charge density, ie. the peptide chain is of mixed character, without the essential hydrophobicity of the linking group as a whole being lost.

An important embodiment of the invention is a single variable domain protein (Dab) attached to a proteinaceous 'tail' which acts as the linking group as defined above, the 'tail' being coupled to a solid surface or to a tracer without significant loss of specific binding activity.

A particularly preferred linking group, especially for use in coupling to a solid plastics surface, comprises the "Myc" amino acid sequence(SEQ ID NO:1):

GLU-GLN-LYS-LEU-ILE-SER-GLU-GLU-ASP-LEU-ASN

The linking group will normally be attached at or near one end of a variable domain protein. Normally, the point of attachment will be the amino terminus of the peptide linking group. This is the left hand end of the sequences A and B as seen in FIG. 2 of the accompanying drawings. Preferably, the variable domain protein(s) and the linking group have been produced together by expression in a genetically modified organism. The is polypeptide linking group may, for example, be synthesised (cloned) together with a variable domain protein and comprise a proteinaceous tail on one end of the domain sequence. The linking group will comprise at least about 5 amino acid residues, to confer sufficient length to "distance" the variable domain from the surface or tracer to which it is linked.

Actual coupling can be achieved, for example, by means of conventional bifunctional chemical cross-linking agents. Preferably, such a chemical coupling site is sufficiently remote, within the linking group, from the variable domain sequence itself that any molecule which becomes coupled to the linking group is held at a distance from the variable domain sequence.

Where the tracer is a protein, such as an enzyme, it is preferably covalently coupled to the linking group via the e-amino group of a lysine residue in the linking group. Examples of suitable enzymes are horse raddish peroxidase, alkaline phosphatase, beta-galactosidase, glucose oxidase and urease.

In one embodiment of the invention, in which the variable domain is attached via the linking group to a solid surface, the surface is a surface of a solid structure formed from plastics material, such as polystyrene, polyvinylchloride (PVC) or polyethylene teraphthalate glycol (PETG). Examples of surfaces to which it would be extremely useful to immobilise variable domains are so-called "latex" particles (which are minute solid particles of plastics material such as polystyrene, generally used in aqueous suspension), and the many other structures formed from plastics material such as beads, pegs and wells, commonly used in immunoassays.

The invention encompasses specific binding reagents composed of a plurality of variable domain proteins. These can be equivalent to natural Fv fragments, ie. a heavy chain variable region with a light chain variable protein, or they can comprise combinations of heavy chain or light chain variable region proteins. Such combinations are normally held together by relatively weak interactions. The linking group of the invention can be incorporated at or near one end of one of the variable region protein sequences, but more than one linking group, of the same or differing character, can be incorporated in the combination if desired, eg. region protein or at or near ends of the different variable region proteins. The individual variable domain proteins can be expressed separately during cloning. Generally they will combine naturally under mild conditions, which do not inhibit the weak interactions that can cause them to associate.

If desired, a reagent of the invention can be made to exhibit specificity for two distinct materials, by comprising a variable domain unassociated with any other substantial portion of its originating antibody, linked, by means of an intervening linking group, to a second variable domain of different specificity also unassociated with any other substantial portion of its originating antibody. Examples of particularly suitable combinations of specificities are anti-analyte and anti-enzyme.

The invention is not concerned in principle with novel ways of producing single domain antibody fragment or novel ways of producing combinations of such fragments with peptide tails. The Ward et al paper discloses methods that are adequate for these purposes. Indeed, Ward et al disclose the production of an anti-lyzozyme single domain antibody fragment having a "Myc" tail. This combination could be used in accordance with the present invention, but Ward et al only contemplate the use of the "Myc" tail as an epitope to assist them in their experimental identification and isolation of the anti-lysozyme Dab that they produced. Ward et al make no suggestion that the "Myc" tail might be ideal for immobilising the Dab on a plastics surface. Neither is this concept disclosed in EP 0368684 A1. Also, neither of these documents mentions the advantage of having a lysine residue in such a peptide tail.

Methods for the production of an activated variable domain fragment, a bispecific reagent containing 2 variable domains of different specificity, and conjugated products containing enzyme labels, in accordance with the invention, are given below purely by way of example.

EXAMPLES

Example 1 a) Preparation of a vector containing the anti-lysozyme $V_H$ fragment D1.3 as a Pst1-BstEII cassette.

The anti-lysozyme $V_H$ fragment D1.3 is excised as a Pst1-BstEII fragment from the expression vector pSW1-VHD1.3-VKD1.3. This vector, and the other expression vector used in this example, pSW1-VHPOLY-TAG1, are fully described by the aforementioned Ward et al (1989) publications.

pSW1-VHPOLY-TAG1 is restricted with Pst1 and BstEII, and the anti-lysozyme Pst1-BstEII $V_H$ fragment of D1.3 is ligated into the opened vector. This ligation creates an expression vector with the $V_H$ D1.3 fragment inserted and is essentially the same as the expression vector pSW1-VHD1.3-TAG1 (Ward et al referred to earlier.), but with the Pst1 and BstEII restriction sites incorporated. We can refer to this expression vector as pVHD1.3-TAG1.

b) Cloning of a linking group sequence downstream of the cloned $V_H$ gene in pVHD1.3-TAG1.

The replacement of TAG1 by a linking group sequence downstream of the $V_H$ gene is done by the technique of site directed mutagenesis with large oligonucleotides as described in Verhoeyen et al., Science (1988), 239, 1534–1536.

Single stranded DNA template is prepared from mpl9VHD1.3-TAG1. This is the HindIII-EcoRI fragment from pVHD1.3-TAG1, containing $V_H$ D1.3 and TAG1, cloned in the HindIII and EcoRI sites of mp19. Single stranded DNA obtained from this clone contains the coding strand of the $V_H$ D1.3-TAG1 sequence. A DNA oligonucleotide is hybridized to the template to serve as primer to polyerize a second DNA strand. This oligonucleotide contains the required linking group sequence flanked on either side by 12 bases homologous to the site of integration. The double stranded molecule is transformed in *E.coli*, where a certain proportion of the molecules is 'repaired' by incorporation of the activation sequence structure. The 12 flanking bases, homologous to the site of integration, are the last four codons of $V_H$ D1.3 and the two stop codons followed by six bases present in pVHD1.3-TAG1. The oligonucleotide replaces the TAG1 gene sequence with that of the linking group gene sequence.

Convenient restriction sites can be incorporated in is the associated oligonucleotide to facilitate manipulation of the DNA sequences.

BRIEF DESCRIPTION OF THE DRAWINGS

FIG. 1 of the accompanying drawings shows three oligonucleotide sequences I, II and III (SEQ ID NO:2, SEQ ID NO:3, and SEQ ID NO:4) useful in the above procedure. Sequences I and II are alternative sequences for producing an identical hydrophylic linking group, and III can be used to produce a hydrophobic linking group.

FIGS. 2A and 2B shows the cDNA and amino acid sequences of two linking groups A and B (SEQ ID NO:5 and 7 and SEQ ID NO:6 and 8). Linking group A is hydrophylic, and can be produced using either of oligonucleotides I and II. Linking group B is hydrophobic, and can be produced using oligonucleotides III.

FIG. 3 shows the calibration curve derived from the HRP conjugates of the Examples.

FIG. 4 shows the calibration curve derived from the biotin conjugates of the Examples.

Three plasmids derived in this manner, in which the linking group sequence structure contains 12 or 11 amino acids (n=1), and designated pVHD1.3-ADI, pVHD1.3-ADII and pVHD1.3-ADIII, are produced using sequences I, II and III. These plasmids are expressed in *E.coli* (as in Ward et al.).

Example 2

Construction of a dual specificity reagent containing two variable domains.

A second $V_H$ domain, of a different specificity from $V_H$ D1.3 and prepared as a DNA fragment using standard recombinant DNA technology, is cloned in the unique Kpn1 restriction site of either pVHD1.3-ADI, pVHD1.3-ADII or pVHD1.3-ADIII. The resulting expression vectors now express $V_H$ D1.3 linked to a $V_H$ domain of different specificity by an amino acid 'bridge' containing a lysine residue to which other materials can be coupled.

Example 3

Conjugation of the protein products derived from pVHD1.3-ADI, pVHD1.3-ADII and pVHD1.3-ADIII.
a) Conjugation of alkaline phosphatase.

100 μl of variable domain fragment protein with associated "tail" (2.5–5.0 mg/ml) is incubated with 100 μl alkaline phosphatase (10 mg/ml) and 5 μl glutaraldehyde (5%) at room temperature for 60 mins. Then 5 ml of Tris/ovalbumin buffer (0.05 M Tris, pH 7.5; 5% ovalbumin) is added and the mixture left at +4° C. for at least 24 hrs. Then the conjugate mixture is tested, quick-frozen and stored in aliquots at low temperature, eg. –20 to –80° C., until use.
b) Conjugation of horse radish peroxidase (HRP):

4 mg of HRP is dissolved in 1 ml distilled water. Then 0.2 ml of freshly prepared 0.1 M $NaIO_4$ is added and the solution stirred for 20 mins. at room temperature. The HRP-aldehyde solution is then dialyzed against 1 mM sodium acetate buffer, pH 4.4, overnight at +4° C. After dialisis the pH of the solution is raised to 9.0–9.5 by adding 20 μl of 0.2 M sodium carbonate buffer, pH 9.5. Immediately 5 mg of the variable domain protein with associated "tail", in 0.01M sodium carbonate buffer, pH 9.5, is added, and the mixture is stirred at room temperature for 2 hrs. Then 0.1 ml of a freshly prepared sodium borohydride solution (4 mg/ml in water) is added and the mixture is left for 2 hrs at +4° C. After this incubation the conjugate mixture is chromato-graphed on a 35×2.5 cm column of Sephacryl S-200, equili-brated in PBS. The absorbance of each fraction (2 ml) is measured at 280 nm and 403 nm and the fractions compris-ing the desired conjugate peak are pooled. Bovine serum albumin is added to a final concentration of 10 mg/ml and aliquots are quick-frozen and stored at a low temperature, eg. –20° C. to –80° C., until use.

Example 4

Monoclonal antibodies having binding specificities to linkers A and B (FIG. 2) are prepared for the purposes of detection of the variable domain fragments in the *E.coli* supernatant, for purification, and for construction of tracer immune complexes. After synthesis of the peptide (eq. by solid phase peptide synthesis) and conjugation macromol-ecules to provide immunogenic character (eg. conjugation to bovine serum albumin or keyhole limpet haemacyanin), monoclonal antibodies can be raised in mice using conven-tional techniques.

Example 5

An immunoassay for lysozyme utilising variable domain antibody fragments with peptide tails
Experimental procedure Anti-lysozyme $V_H$ fragments were produced as described in Example 1 and Ward et al (1989). Samples of fragments were prepared either with or without tails; two types of tail were used, one hydrophilic and the other hydrophobic, with sequences A and B respectively as shown in FIG. 2. Two conjugates were made from each of the three types of fragment, one conjugate with biotin and the other with horse radish peroxidase (HRP).
a) Conjugation with HRP. The method of Example 3b was followed, but using 0.042 mg of fragment for each conju-gate.
b) Conjugation with biotin. A solution of fragment (0.5ml) at a concentration of 80 μg/ml (+/–10 μg/ml) was dialysed against carbonate buffer, pH 9.5. Biotin-N-hydroxysuccinimide (biotin-NHS, Sigma) was dissolved in dimethyl sulphoxide at a concentration of 1 mg/ml, and 75 μl of this was added to the dialysed solution of fragment. The reaction mixture was stirred and then left to stand at ambient temperature for two hours, after which the volume was made up to 2.5 ml with phosphate buffered saline, pH 7.2 (PBS). The diluted mixture was passed down a disposable gel filtration column (Pharmacia, PD10) to separate any unre-acted biotin-NHS and unconjugated biotin from the conju-gated fragments. Fractions containing the fragments were collected, pooled and dialysed against 2 litres of PBS for 24 hours at 4° C.
c) Preparation of solid-phase. Wells of a commercially-available polystyrene microtitre plate were dosed with looul aliquots of a solution of lysozyme at 100 μg/ml in PBS. The dosed plate was incubated at 37° C. for 2 hours to allow efficient adsorption of the lysozyme onto the polystyrene surface. The plates were washed 5 times in PBS containing Tween 20 (0.15% V/V, PBST) and were then treated with a 2% solution of skimmed milk protein (W/V), 150 μl per well, in PBS for a further 2 hours at 37° C. This second treatment was to block (with milk proteins) any unoccupied sites on the well surface with potential for protein adsorption, to minimise subsequent non-specific adsorption of assay components.
d) Generation of a standard curve for the lysozyme assay. A series of lysozyme calibration standards were prepared by dilution of a stock solution of lysozyme into appropriate volumes of PBST with 1% boving serum albumin (BSA, W/V), to give concentrations of $2\times10^{-6}$M, $2\times10^{-7}$M, $2\times10^{-8}$M and $2\times10^{-9}$M and $2\times10^{-10}$M. Working strength solutions of the conjugates were prepared by diluting the conjugate stock solutions to ⅟₂₅ for the biotin conjugate and ⅟₅₀ for the HRP conjugate. Microtitre plates sensitised as in (c) were washed 5 times in PBST before appropriately labelled wells were dosed with equal volumes of conjugate and calibration standards (100 μl, total per well). This competitive binding assay step was continued for 1 hour at 37° C., after which the wells were washed 5 times in PBST.

For the procedure using biotin conjugates, the wells were dosed with a solution of streptavidin/alkaline phosphase conjugate (Sigma) and incubated at 37° C. for a further hour. The plate was washed 5 times again, and then dosed with Sigma 104 phosphatase substrate in 1M diethanolamine buffer, pH 9.8, at 1 mg/ml. Colour development was continued for 10 to 15 minutes at ambient temperature before the optical densities were read.

For the procedure using HRP conjugates, the wells were immediately dosed with a solution of tetramethylbenzidine (TMB) in phosphate citrate buffer, pH 6.5 and colour development was continued for 10–15 minutes at ambient temperature. Each well was dosed with 50 µl of 2M HCl before the optical densities were determined.

Results

The calibration curves derived from the HRP conjugates are shown in FIG. 3 and those from the biotin conjugates in FIG. 4. In each figure it can be seen that the conjugate of $V_H$ with no tail fails to give a satisfactory calibration curve, whilst the fragments with either tail gave acceptable results, clearly showing the benefit of an appropriate linking group.

Example 6

Efficiency of $V_H$ fragments in sensitising plastics surfaces—the effect of different peptide tails Experimental procedure Anti-lysozyme $V_H$ fragments were produced as described in Example 1 and Ward et al (1989), either alone or with a peptide tail. The two tail sequences A and B as in FIG. 2, and a third tail, identical to the "Myc" peptide as described by Ward et al (Nature, 1989, vol. 341 p.544–546), were used. The amino acid sequence (SEQ ID NO:1) of this "Myc" peptide is as follows:

GLU-GLN-LYS-LEU-ILE-SER-GLU-GLU-ASP-LEU-ASN

Solutions of these fragments were used to sensitise wells of a microtitre plate by simple adsorption. The efficiency with which these fragments bound to the plastic surface, whilst still retaining their ability to specifically bind lysozyme, was assessed by means of subsequent immunochemical binding of a lysozyme/horse radish peroxidase (HRP) conjugate.

a) Conjugation of lysozyme with HRP. The method of Example 3b was followed, with purified lysozyme being used in place of activated $V_H$.

b) Preparation of solid-phase. Wells of a microtitre plate (Costar "fastbinder" made with polyethylene teraphthalate glycol) were dosed with 100 ul aliquots of $V_H$ fragments in carbonate buffer, pH 9.8 at a concentration of 80 ng/ml. Some wells were treated with carbonate buffer to provide an unsensitised control. The dosed plate was incubated at 37° C. for 2 hours to allow efficient adsorption of the peptides onto the well surface.

c) Assessment of lysozyme capture efficiency. The wells of the sensitised plate were emptied and washed 5 times in phosphate buffered saline, pH 7.2, containing 0.15% Tween 20 (v/v, PBST). Each well was treated with a solution of lysozyme/HRP conjugate (diluted 1/100 from stock solution, see Example 3b) in PBST containing 1% (w/v) bovine serum albumin. This immunochemical binding (or capture) step was continued for 1 hour at 37° C., after which the plate was emptied and washed 5 times again in PBST. The wells were dosed with a solution of tetramethylbenzidine in phosphate citrate buffer, pH 6.5, and the whole plate was maintained at ambient temperature until adequate colour had developed. At this point, 50 µl of 2M HCL was added to each well and the optical densities were determined.

Results

The mean optical densities produced from each type of sensitisation are shown in Table 1. The capture efficiency of solid phases produced by adsorption of fragments with various peptide tails onto the PETG wells is proportional to the measured optical density.

TABLE 1

| | Mean optical density: | |
|---|---|---|
| Tail type | Sensitized wells | Control wells |
| no tail | 0.09 | 0.05 |
| Myc tail | 0.84 | 0.06 |
| hydrophobic | 0.44 | 0.07 |
| hydrophilic | 0.12 | 0.06 |

These results clearly show the practical benefit of adding appropriate linker groups to fragments with immunochemical binding activity. Surprisingly, charged peptides containing short hydrophobic regions (of the Myc type) are the most efficient at these economical, low concentrations.

Similar results, demonstrating the advantage of hydrophobic linking groups, were obtained using commercially-available wells made from polystyrene and from polyvinylchloride.

What is claimed is:

1. A specific binding reagent, comprising:
   (i) at least one variable domain antibody fragment which is essentially free from the rest of the originating antibody or antibodies;
   (ii) a peptide linking group, which does not contribute to the specific binding properties of the reagent, said peptide linking group being attached at or near the end of the variable domain antibody fragment and wherein said linking group comprises from 5 to 20 amino acid residues, is hydrophobic and includes at least one lysine residue and at least two amino residues selected from the group consisting of valine, leucine, isoleucine, phenylalanine, tyrosine, tryptophan, proline and alanine and
   (iii) a solid surface or a tracer, coupled via the lysine residue of the linking group by covalent attachment to the variable domain antibody fragment.

2. A specific binding reagent according to claim 1, consisting of a single variable domain antibody fragment attached to a proteinaceous 'tail' which acts as the linking group, the 'tail' being coupled to a solid surface or to a tracer without significant loss of specific binding activity.

3. A specific binding reagent according to claim 1, wherein the linking group comprises the amino acid sequence:
   set forth in SEQ ID NO:1.

4. A specific binding reagent according to claim 1, wherein the variable domain antibody fragment and the linking group have been produced together by expression in a genetically modified organism.

5. A specific binding reagent according to claim 1, wherein the solid surface is a surface of a solid structure formed from plastics material.

6. A specific binding reagent according to claim 1, wherein the solid surface is the surface of a latex particle.

7. A specific binding reagent according to claim 1, wherein the tracer is a protein, covalently coupled to the linking group via the e-amino group of a lysine residue in the linking group.

8. A specific binding reagent according to claim 5, wherein the protein is an enzyme.

9. A specific binding reagent according to claim 5 or claim 6, wherein the linking group contains at least two adjacent amino acid residues conferring hydrophobicity on the linking group.

10. The method of preparing a specific binding reagent according to claim 1 which comprises using a hydrophobic polypeptide containing from 5 to 20 amino acid residues as a linking group to attach to a solid surface a specific binding entity comprising at least one variable domain protein which is essentially free from any originating antibody or antibodies.

11. The method of preparing a specific binding reagent according to claim 1 which comprises using a polypeptide containing from 5 to 20 amino acid residues, and wherein at least two adjacent amino acid residues confer hydrophobicity on the polypeptide, as a linking group to attach a solid surface a specific binding entity comprising at least one variable domain protein which is essentially free from any originating antibody or antibodies.

12. A method according to claim 10 or claim 11, wherein the specific binding entity is a Fv or Dab antibody fragment.

13. A method according to any one of claims 9 to 11 wherein the polypeptide has the amino acid sequence:
   set forth in SEQ ID NO:1.

14. In an immunoassay using a specific binding reagent, the improvement which comprises using, as said specific binding reagent, the reagent of claim 1.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 11 amino acids
       (B) TYPE: amino acid
       (D) TOPOLOGY: linear (xi) SEQUENCE DESCRIPTION: SEQ ID NO:1:

Glu Gln Lys Leu Ile Ser Glu Glu Asp Leu Asn (2) INFORMATION FOR SEQ ID NO:2:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO:2:

```
TAGCCCTTAT TACAGGTACC CCTTACCGGA ATTCCCNGGA TCCTGAGGAG ACGGT      55
```

(2) INFORMATION FOR SEQ ID NO:3:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO:3:

```
TAGCCCTTAT TACTTCAGGT ACCCCTTACC GGAGTTCCCN GGATCCTGAG GAGACGGT   58
```

(2) INFORMATION FOR SEQ ID NO:4:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:4:

```
TAGCCCTTAT TAGGGTACCA AAAGCTTCGC NTACCGCGGC TGAGGAGACG GT         52
```

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (xi) SEQUENCE DESCRIPTION: SEQ ID NO:5:

```
GGATCCNGGG AACTCCGGTA AGGGGTACCT G                               31
```

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..33

(xi) SEQUENCE DESCRIPTION: SEQ ID NO:6:

```
GCCGCGGTAN GCGAAGCTTT TGGTACCC                                   28
```

(2) INFORMATION FOR SEQ ID NO:7:

(i) SEQUENCE CHARACTERISTICS:
        (A) LENGTH: 11 amino acids
        (B) TYPE: amino acid
        (D) TOPOLOGY: linear

```
                               -continued (xi) SEQUENCE DESCRIPTION: SEQ ID NO:7:

Gly Ser Xaa Gly Asn Ser Gly Lys Gly Tyr Leu
1               5                   10

(2) INFORMATION FOR SEQ ID NO:8:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO:8:

Ala Ala Val Xaa Ala Lys Leu Leu Val Pro
1               5                   10
```